United States Patent
Bustan et al.

(10) Patent No.: US 9,757,182 B2
(45) Date of Patent: Sep. 12, 2017

(54) IDENTIFICATION AND VISUALIZATION OF GAPS BETWEEN CARDIAC ABLATION SITES

(71) Applicant: BIOSENSE WEBSTER (ISRAEL) LTD., Yokneam (IL)

(72) Inventors: Itamar Bustan, Zichron Ya'acov (IL); Michael Timofeyev, Nesher (IL); Akram Zoabi, Kfar Masser (IL); Noam Seker Gafni, Kiryat Tivon (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 340 days.

(21) Appl. No.: 14/293,400

(22) Filed: Jun. 2, 2014

(65) Prior Publication Data
US 2015/0342662 A1 Dec. 3, 2015

(51) Int. Cl.
| A61B 18/12 | (2006.01) |
| A61B 34/10 | (2016.01) |
| A61B 18/00 | (2006.01) |
| A61B 34/20 | (2016.01) |

(52) U.S. Cl.
CPC .............. *A61B 18/12* (2013.01); *A61B 34/10* (2016.02); *A61B 34/20* (2016.02); *A61B 2018/00577* (2013.01); *A61B 2018/00839* (2013.01); *A61B 2018/00898* (2013.01); *A61B 2034/107* (2016.02); *A61B 2034/2051* (2016.02)

(58) Field of Classification Search
CPC . A61B 18/12; A61B 18/1492; A61B 18/1206; A61B 2018/00577; A61B 2018/00839; A61B 2018/00898; A61B 34/10; A61B 34/20; A61B 2034/107; A61B 2034/2051
See application file for complete search history.

(56) References Cited

U.S. PATENT DOCUMENTS

| 5,391,199 | A | 2/1995 | Ben Haim | |
| 5,722,403 | A * | 3/1998 | McGee | A61N 1/44 600/373 |
| 5,941,251 | A * | 8/1999 | Panescu | A61B 5/0066 128/899 |
| 6,239,724 | B1 | 5/2001 | Doron | |
| 6,332,089 | B1 | 12/2001 | Acker | |
| 6,484,118 | B1 | 11/2002 | Govari | |
| 6,618,612 | B1 | 9/2003 | Acker | |
| 6,690,963 | B2 | 2/2004 | Ben Haim | |
| 7,001,282 | B1 | 2/2006 | Jennings | |
| 7,232,437 | B2 * | 6/2007 | Berman | A61B 18/22 600/374 |

(Continued)

FOREIGN PATENT DOCUMENTS

| EP | 1070480 A2 | 1/2001 |
| EP | 1922055 | 3/2007 |

(Continued)

*Primary Examiner* — Michael Peffley
(74) *Attorney, Agent, or Firm* — Louis J. Capezzuto

(57) ABSTRACT

A method includes receiving locations of multiple ablation sites formed on a surface of a heart. Distances are measured among at least some of the ablation sites based on the locations. One or more gaps between the ablation sites, which meet an alerting criterion, are identified. The identified gaps are indicated to an operator.

18 Claims, 4 Drawing Sheets

(56) References Cited

U.S. PATENT DOCUMENTS

| | | | | |
|---|---|---|---|---|
| 7,598,088 | B2* | 10/2009 | Balas | A61B 1/303 |
| | | | | 436/164 |
| 8,403,925 | B2* | 3/2013 | Miller | A61B 18/1233 |
| | | | | 606/34 |
| 8,876,817 | B2* | 11/2014 | Avitall | A61B 18/1492 |
| | | | | 606/34 |
| 9,014,789 | B2* | 4/2015 | Mercader | A61B 5/1459 |
| | | | | 600/407 |
| 9,192,789 | B2* | 11/2015 | Thapliyal | G06F 19/321 |
| 2002/0065455 | A1 | 5/2002 | Ben Haim | |
| 2003/0120150 | A1 | 6/2003 | Govari | |
| 2004/0068178 | A1 | 4/2004 | Govari | |
| 2004/0147920 | A1* | 7/2004 | Keidar | A61B 5/06 |
| | | | | 606/34 |
| 2008/0172049 | A1 | 7/2008 | Bredno | |
| 2013/0116881 | A1 | 5/2013 | Bogema | |

FOREIGN PATENT DOCUMENTS

| | | |
|---|---|---|
| EP | 2662049 A2 | 11/2013 |
| WO | WO 96/05768 | 2/1996 |
| WO | WO 2007/029154 | 3/2007 |

* cited by examiner

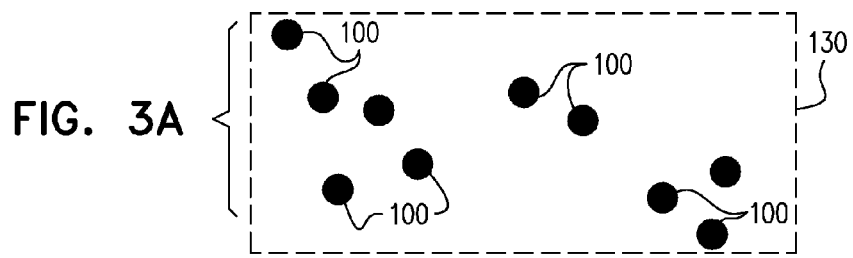
FIG. 3A
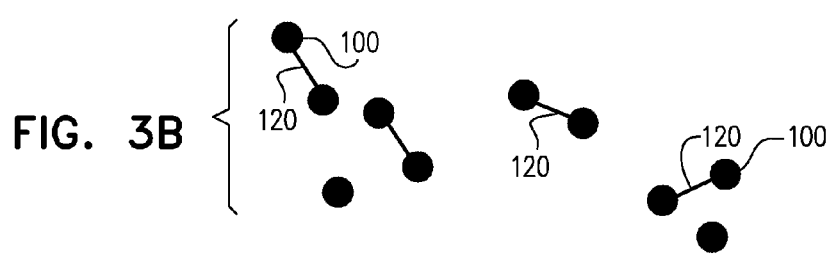
FIG. 3B
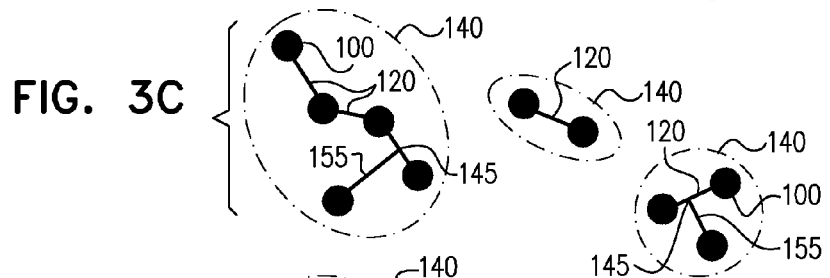
FIG. 3C
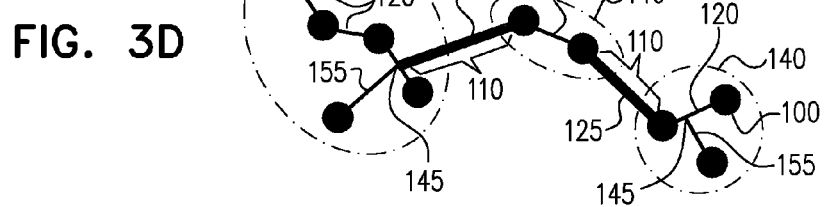
FIG. 3D
FIG. 3E
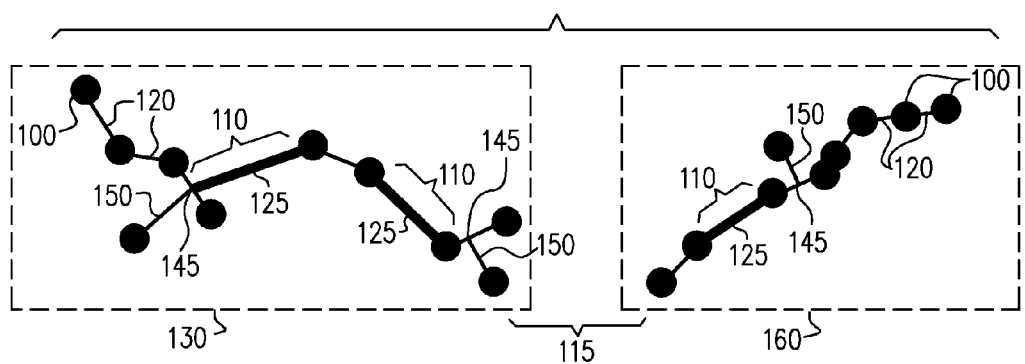

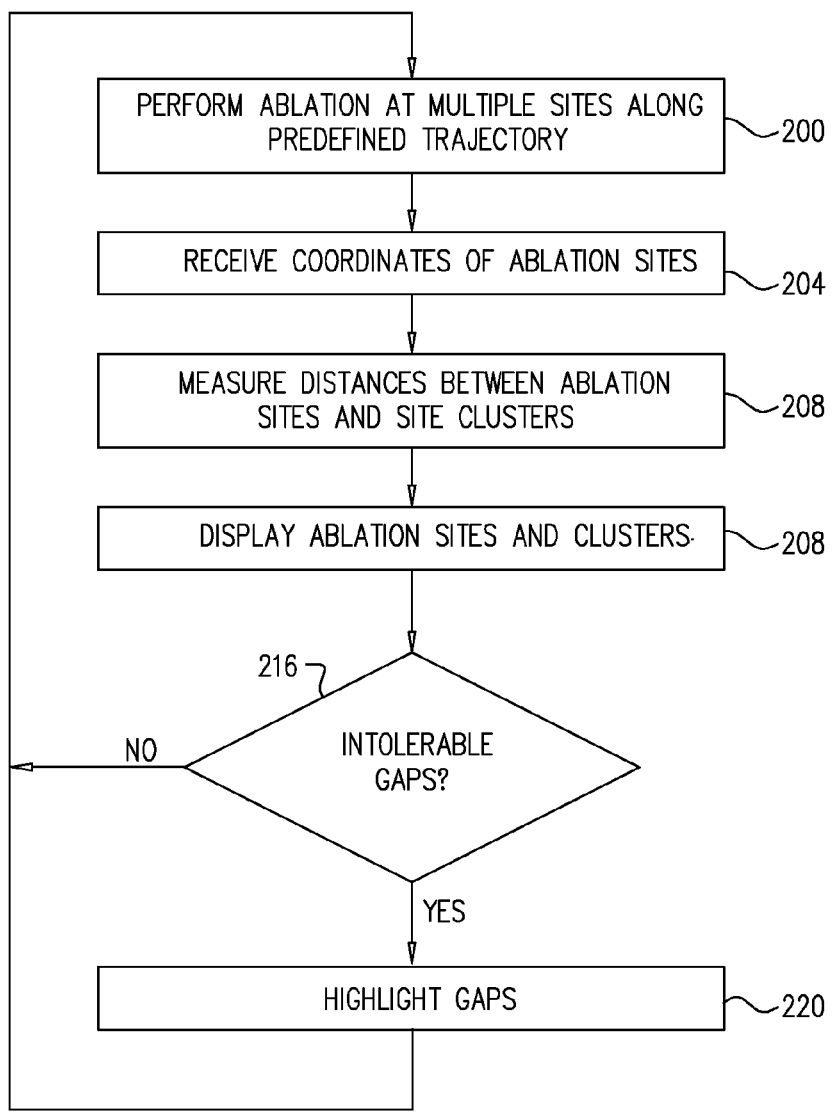

IDENTIFICATION AND VISUALIZATION OF GAPS BETWEEN CARDIAC ABLATION SITES

FIELD OF THE INVENTION

The present invention relates generally to cardiac ablation, and particularly to methods and systems for mapping cardiac ablation sites.

BACKGROUND OF THE INVENTION

Radio-Frequency (RF) ablation is a common procedure for treating various cardiac disorders. Various ablation techniques, and methods for visualizing the ablation procedure, are known in the art. For example, U.S. Patent Publication 2013/0116881, whose disclosure is incorporated herein by reference, describes a system which provides heart ablation unit control. The system includes an input processor for acquiring electrophysiological signal data from multiple tissue locations of a heart and data indicating tissue thickness at the multiple tissue locations. A signal processor processes the acquired electrophysiological signal data to identify location of particular tissue sites of the multiple tissue locations exhibiting electrical abnormality in the acquired electrophysiological signal data and determines an area of abnormal tissue associated with individual sites of the particular sites. An ablation controller automatically determines ablation pulse characteristics for use in ablating cardiac tissue at an individual site of the particular tissue sites in response to the acquired data indicating the thickness of tissue and determined area of abnormality of the individual site.

U.S. Pat. No. 7,001,383, whose disclosure is incorporated herein by reference, describes a method for ablating tissue in a heart of a subject during an ablation procedure. The method includes applying a local treatment to the heart at a plurality of sites designated for ablation. At each respective site, a parameter is sensed that is indicative of a level of ablation at the site. The method preferably includes displaying a map of the heart, and designating, on the map, during the ablation procedure, indications of the respective levels of ablation at the sites, responsive to the respective sensed parameters.

U.S. Patent Publication 2008/0172049, whose disclosure is incorporated herein by reference, describes an apparatus and method for ablating tissue in a heart of a subject during an ablation procedure. The method includes contacting an ablation catheter tip to tissue of the heart at a plurality of sites designated for ablation; sensing at each respective site a feedback signal from the ablation catheter indicative of success of the intended local ablation; storing any available data defining a current position of the ablation catheter tip relative to the heart at a moment of sensing the feedback signal indicative of a failed intended ablation for later re-visit; displaying a map of a region of interest of the heart; and designating, on the map display, indications of the sites corresponding to when the required electrical current is above the threshold current value indicative of a gap in an ablation line or ring.

SUMMARY OF THE INVENTION

An embodiment of the present invention that is described herein provides a method including receiving locations of multiple ablation sites formed on a surface of a heart. Distances among at least some of the ablation sites are measured based on the locations. One or more gaps between the ablation sites, which meet an alerting criterion, are identified. The identified gaps are indicated to an operator.

In some embodiments, identifying the gaps includes detecting the gaps that are larger than a first threshold but smaller than a second threshold. In other embodiments, measuring the distances includes scaling a distance between first and second ablation sites by a scaling factor that depends on an ablation quality associated with one or both of the first and second ablation sites.

In some embodiments, measuring the distances includes clustering the ablation sites into groups by connecting adjacent ablation sites whose distances are smaller than a first threshold, and identifying the gaps includes identifying separations between groups that are smaller than a second threshold. In other embodiments, clustering the ablation sites includes iteratively calculating the distances from a given cluster to one or more of the ablation sites, and adding an ablation site to the given cluster upon finding that a distance from the ablation site to the given cluster is smaller than the first threshold.

In some embodiments, measuring the distances includes assessing the distances depending on parameters of an ablation signal used for forming the ablation sites. In other embodiments, measuring the distances includes assessing the distances depending on sizes of the ablation sites.

There is also provided, in accordance with an embodiment of the present invention, a system including an interface and a processor. The interface is configured to receive locations of multiple ablation sites formed on a surface of a heart. The processor is configured to measure distances among at least some of the ablation sites based on the locations, to identify one or more gaps between the ablation sites that meet an alerting criterion, and to indicate the identified gaps to an operator.

The present invention will be more fully understood from the following detailed description of the embodiments thereof, taken together with the drawings in which:

BRIEF DESCRIPTION OF THE DRAWINGS

FIGS. 3A-3E are diagrams illustrating a method for detecting and visualizing ablation gaps, in accordance with an embodiment of the present invention; and FIG. 4 is a flow chart illustrating a method for detecting and visualizing ablation gaps, in accordance with an embodiment of the present invention.

DETAILED DESCRIPTION OF EMBODIMENTS

Overview

Cardiac ablation is a procedure that locally heats and ablates cardiac tissue on the inner surface of a heart cavity so as to relieve cardiac dysfunction. As a physician, typically a cardiologist, performs the ablation therapy, the physician typically forms ablation lesions by applying RF energy, for example, to the heart tissue using an ablation electrode positioned at a distal end of a catheter. The ablation electrode contacts the endocardium in the heart cavity at multiple discrete ablation sites along a predefined trajectory.

The cardiologist may monitor the procedure by observing the position of the catheter tip in an image of the heart on a display. The catheter tip position can be detected, for example, by a catheter position tracking system or imaging system.

If the cardiologist creates adjacent ablation lesions that are too far apart, the resulting gap may not completely eliminate the parasitic electrical pathways of the cardiac activation wave, for example, and the cardiac dysfunction may not be completely alleviated.

Embodiments of the present invention described herein provide methods for identifying and visualizing gaps between cardiac ablation sites. In some embodiments, a processor of a cardiac mapping and ablation system receives the coordinates of multiple ablation sites on the surface of the heart. The processor then identifies intolerable gaps between ablation sites, e.g., gaps that are larger than a certain threshold. The processor presents the identified gaps, so as to enable the physician to eliminate them.

In some embodiments, the processor identifies the intolerable gaps using an iterative process that measures distances between ablation sites and progressively clusters ablation sites into groups. The process typically presents the resulting groups or clusters, and emphasizes any intolerable gaps found between them.

Using the disclosed technique, the physician is provided with a clear real-time visual display that highlights locations where ablation quality is likely to be insufficient. Using such a display, the physician is able to revisit the locations in question and complete the ablation procedure successfully.

SYSTEM DESCRIPTION

Figure 1:
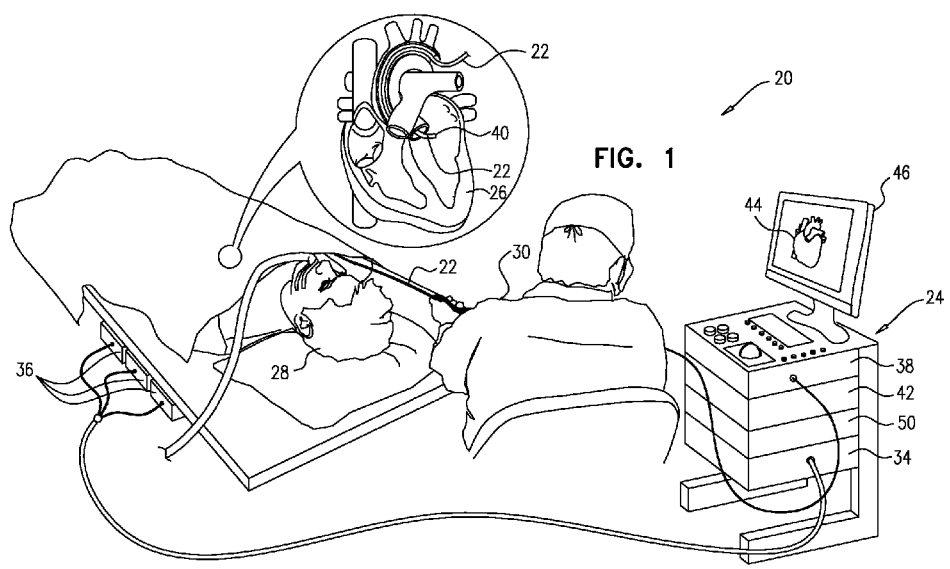
FIG. 1 is a block diagram that schematically illustrates a system for cardiac ablation, in accordance with an embodiment of the present invention.

FIG. 1 is a block diagram that schematically illustrates a system 20 for cardiac ablation, in accordance with an embodiment of the present invention. System 20 comprises a probe 22, in the present example a cardiac catheter, and a control console 24. In the embodiment described herein, it is assumed by way of example that catheter 22 is used for the ablation of tissue in a heart 26 in a patient 28 using an ablation electrode positioned near a distal end 40 of catheter 22. Alternatively or additionally, catheter 22 may be used any other suitable diagnostic and/or therapeutic procedure such as electro-physiological (EP) cardiac signal mapping of a cavity of heart 26 of patient 28 for the diagnosis of cardiac dysfunctions (not shown here).

Console 24 comprises a processor 42, typically a general-purpose computer, with suitable front end circuitry for receiving signals from probe 22 via an interface 38 and for controlling the other components of system 20 described herein. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

An operator 30, typically a physician or cardiologist, inserts catheter 22 into patient 28 and navigates the catheter through the patient's vascular system. Cardiologist 30 moves distal end 40 of catheter 22 in the vicinity of the target region in heart 26 for ablation.

First, relating to sensing and recording the position (i.e. coordinates) of the ablation electrode at distal end 40 in patient 28 during ablation therapy, a position sensing system is may be used to measure the position of distal end 40 of catheter 22 in the heart cavity in some embodiments. Console 24 comprises a driver circuit 34, which drives magnetic field generators 36 placed at known positions external to patient 28, e.g., below the patient's torso.

A magnetic field sensor, typically comprising coils (not shown), is attached to catheter 22 near distal end 40. The position sensor generates electrical position signals in response to the magnetic fields from the coils, thereby enabling processor 42 to determine the coordinates, or position, of distal end 40 within the heart cavity, and thus the coordinates of the ablation electrode.

In other embodiments, system 20 may use impedance-based position sensing techniques (e.g., advanced catheter location (ACL) technologies) to determine the position of distal end 40 within the heart cavity. System 20 in these embodiments is configured to drive current between at least one current electrode at distal end 40 and a plurality of body surface electrodes on patient 28 (not shown in FIG. 1) typically attached to the patient's chest above the heart. Processor 42 then determines the position of the distal end based on the measured currents between the plurality of body surface electrodes and the at least one current electrode at distal end 40. Further alternatively, system 20 may determine the position of distal end 40 (and thus of the ablation electrode) in any other suitable way.

Relating to RF ablation, console 24 also comprises an RF signal generator, which is used to apply an RF signal to the ablation electrode at distal end 40 of catheter 22. When the electrode contacts the heart tissue, the RF signal locally heats and induces a local necrosis of the heart tissue at the ablation site. The position sensing system, or an imaging system such as ultrasound, fluoroscopy, or magnetic resonance imaging (MRI), for example, records the position of the multiple ablation sites formed by the ablation electrode during the procedure.

Processor 42 displays an image 44 of heart 26 with the recorded positions of the multiple ablation sites, possibly overlaid with local electro-cardiac signal measurements on the simulated surface, to cardiologist 30 on a display 46.

Interface 38 is configured to relay the coordinates of the multiple ablation sites formed by the ablation electrode to processor 42. In some embodiments, the interface may be configured to receive signals from the magnetic field sensor signals indicative of the coordinates of the ablation electrode positioned near distal end 40 of catheter 22. Processor 42 then computes the position of distal end 40 (e.g., the position coordinates of the ablation electrode).

In other embodiments, the interface may be configured to receive the coordinates of the ablation sites recorded by any suitable imaging system (e.g., ultrasound, fluoroscopy, MRI, etc.). Processor 42 may receive the coordinates of the multiple ablation sites by any suitable method in order to use the coordinates to identify ablation gaps as per the embodiments described herein.

Finally, system 20 may also comprise EP cardiac signal mapping, which may be used to assess the effectiveness of the ablation therapy in real time. Catheter 22 may also comprise one or more mapping electrodes near the catheter distal end to measure electro-cardiac signals at one or more respective contact points with the heart tissue. Processor 42 uses the position of distal coordinates of the map points to construct a simulated surface of the cardiac cavity, or chamber, in question. Processor 42 then combines the electrical potential measurements of the map points with the simulated surface to produce a map of the potentials overlaid on the simulated surface. System 20 may use fluoroscopy, or magnetic resonance imaging (MRI), for example, to synchronize images of the heart with the EP mapping in the catheter position sensing system.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239, 724, 6,618,612 and 6,332,089, in PCT Patent Publication WO 1996/05768, and in U.S. Patent Application Publications 2002/0065455, 2003/0120150 and 2004/0068178, whose disclosures are all incorporated herein by reference. The VisiTag™ module, produced by Biosense Webster Inc. (Diamond Bar, Calif.), provides a visual representation of the ablation lesions to assist the cardiologist in ablation strategy by displaying different parameters of the lesion formation.

The embodiments shown in FIG. 1 are merely for visual clarity and not by way of limitation of the embodiments of the present invention. System 20 is not limited to RF ablation, which is used throughout as an example herein. Any other suitable cardiac ablation therapy, such as focused laser ablation or ultrasound ablation may be used. Catheter 22 is not limited to one ablation electrode positioned at distal end 40, but may comprise any suitable number of ablation electrodes positioned at any suitable positions along the body of catheter 22. The catheter may comprise, for example a lasso catheter having multiple ablation electrodes distributed along its distal end.

Identifying Gaps in the Cardiac Ablation Sites

During the ablation procedure, cardiologist 30 typically ablates the cardiac tissue discretely, site-by-site, using the ablation electrode. In some cases, cardiologist 30 may miss a region in the cardiac tissue during ablation along the planned spatial trajectory of the ablation sites, the missed region referred to herein as a gap. If gaps are present, the cardiac dysfunction may not be alleviated by the procedure. Hence, identifying gaps between the ablation lesions and alerting the cardiologist are highly beneficial in assisting the cardiologist in assessing the overall effectiveness of the ablation procedure, and improving it as needed.

Figure 2A:
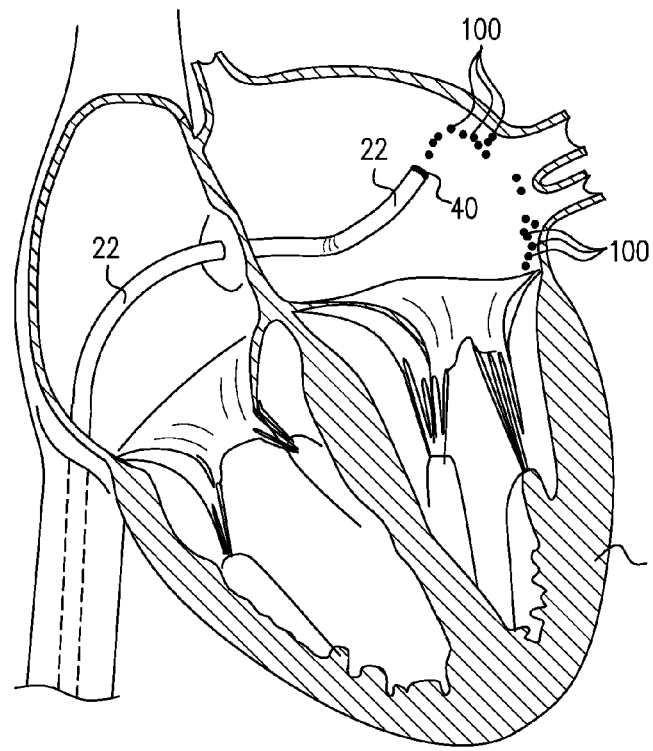
FIG. 2A is a diagram illustrating a heart undergoing ablation, in accordance with an embodiment of the present invention.

FIG. 2A is a diagram illustrating heart 26 undergoing ablation, in accordance with an embodiment of the present invention. The ablation electrode at distal end 40 (shown in black in FIG. 2A) of catheter 22 contacts the heart cavity at multiple ablation sites 100 to induce local necrosis of the heart tissue. A lesion is formed at each ablation site 100.

Using position tracking of a position sensor at distal end 40, or imaging systems as described previously, processor 42 records the positions of multiple ablation sites 100 as cardiologist 30 forms the multiple lesions on the surface of the heat cavity with the ablation electrode. The position of ablation sites 100 can be displayed to cardiologist 30 in real time on image 44 of heart 26 on display 46. EP mapping electrodes near the distal end of catheter 22 or on a separate catheter (not shown in FIG. 1) can be used to monitor changes in the electro-cardiac signals measured at the one or more mapping electrodes as described previously in response to the ablation therapy.

Figure 2B:
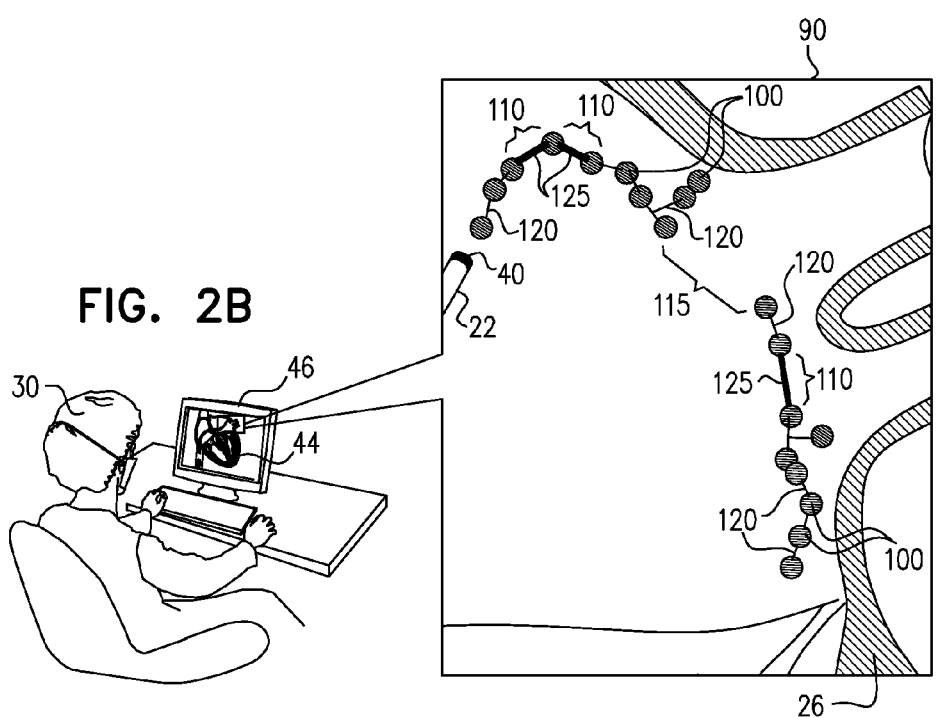
FIG. 2B is a diagram illustrating annotated ablation sites on an image of a heart, in accordance with an embodiment of the present invention.

FIG. 2B is a diagram illustrating annotated ablation sites 100 on image 44 of a heart 26, in accordance with an embodiment of the present invention. FIG. 2B shows an enlarged view of the ablation region in FIG. 2A in an inset 90 of ablation sites 100 after processing by processor 42. An example algorithm for producing this view is described in FIGS. 3A-3E below.

The example of FIG. 2B shows ablation sites 100 as circles. Some of the ablation sites are connected by lines 120. Each group of ablation sites 100 that are interconnected by lines 120 is referred to as a site group or cluster. Intolerable gaps 110 between ablation sites are marked in FIG. 2B with bold lines 125 (and highlighted accordingly to the physician).

In the present embodiment, an intolerable gap is defined as a separation between ablation sites or clusters that is larger than an Adjacent Distance Threshold (ADT) but smaller than an Out Of Group (OOG) threshold. The rationale behind this dual threshold scheme is that very large gaps (>OOG) are likely to be intentional. As such, separations that are larger than the OOG threshold are not considered intolerable gaps, and are typically not highlighted to the physician. An example of such a separation is shown in the figure as a bracket 115.

The diagrams of FIGS. 2A and 2B are depicted merely for conceptual clarity and not by way of limitation of the embodiments of the present invention. The lengths of ADT bracket 110 and OOG bracket 115 (e.g., the values of these parameters) are merely by way of example, and can be chosen by the cardiologist to be any suitable value. Typical values of ADT and OOG (e.g., ADT bracket 110 and OOG bracket 115) are 5 mm and 20 mm, respectively.

Note that in FIG. 2B, the diameters of the lesions at multiple ablation sites 100 formed by the ablation electrode at distal end 40 of catheter 22 are shown to be roughly of the same diameter, for the sake of clarity. In alternative embodiments, the diameters of ablation sites 100 may differ from one another, for example depending on the ablation parameters (e.g., ablation time or ablation signal power) set for each ablation site.

In some embodiments, the distances measured between ablation sites 100 (e.g., lines 120) do not consider the site diameter. For example, the distances may be computed between the ablation site centers. In other embodiments, the distances measured between ablation sites 100 depend on the site diameters. For example, for the same ablation site centers, the distance between large-diameter lesions are smaller than the distance between small-diameter lesions.

In some embodiments, processor 42 scales the measured physical distance between ablation sites by a scaling factor that depends on the ablation quality (also referred to as ablation index) of one or both of the ablation sites. As a result, low-quality ablation sites will be interpreted as being further apart than high-quality sites.

FIGS. 3A-3E are diagrams illustrating an algorithmic flow for detecting and visualizing ablation gaps, in accordance with an embodiment of the present invention. In FIG. 3A, processor 42 receives and registers the positions of multiple ablation sites 100.

In the first step of the algorithm flow, processor 42 examines a certain region 130. For each ablation site 100, the processor searches for the closest neighbor ablation site which does not have a closer neighbor. If the distance between the two ablation sites is smaller than the adjacent distance threshold (ADT), processor 42 flags them as pairs. These distances are connected with lines 120 as shown in FIG. 3B. At the end of the first step, all of ablation sites 100 are either grouped into connected pairs or remain unpaired. Note that this step does not inherently mark every pair of ablation sites that are closer than the ADT threshold.

In the second step of the algorithm, processor 42 connects the clusters (including unpaired individual sites 100 that are regarded as single-site clusters) that are closer to one another than the ADT threshold. This step is shown in FIG. 3C. In this step, some of the distances 155 (between a single-site cluster and a multi-site cluster) are computed between sites 100 and intermediate points 145 on lines 120. This clustering process typically continues until reaching stability, i.e., until it is impossible to find new pairs of clusters to connect. The algorithm step of FIG. 3C produces multiple clusters 140 that are separated from one another by at least the ADT threshold (since otherwise they would have been connected).

In the third and last step, shown in FIG. 3D, processor 42 identifies gaps 110 between adjacent clusters 140, which are smaller than the OOG threshold. The identified gaps are marked with bold lines or otherwise highlighted on display 46 as intolerable gaps 125.

Gaps between ablation site clusters that are separated by more than the OOG threshold are typically not marked and not considered intolerable gaps. FIG. 3E demonstrates a scenario of this sort. The figure shows two regions 130 and 160. The separation between the nearest clusters in the two regions (marked as a gap 115) is larger than the OOG threshold. As such, gap 115 is not marked and not considered intolerable.

The diagrams shown in FIGS. 3A-3E are depicted merely for conceptual clarity in illustrating the disclosed techniques, and not by way of limitation of the embodiments of the present invention. In alternative embodiments, processor 42 may use any other suitable algorithm for identifying gaps 125. For example, any suitable reference points based on the coordinates of multiple ablation sites 100 can be used in computing distances between adjacent ablation sites for identifying gaps. The disclosed techniques are not limited to the center-to-center distance or intermediate points 145 as described previously.

FIG. 4 is a flow chart illustrating a method for detecting the presence of ablation gaps, in accordance with an embodiment of the present invention. The method begins with physician 30 performing ablation at multiple ablation sites 100 along a desired trajectory on the inner surface of heart 26, at an ablation step 200. At a location input step 204, processor 42 receives via interface 38 the locations (e.g., coordinates) of ablation sites 100. As noted above, the locations of ablation sites 100 may be received from any suitable source, such as from a magnetic position tracking system or an imaging (e.g., ultrasound) system.

At a distance measurement step 208, processor 42 measures the distances between ablation sites and/or site clusters, as demonstrated by FIGS. 3A-3E above. At a site displaying step 208, processor 42 displays the clustered ablation sites on display 46.

At a gap checking step 216, processor 42 checks for the presence of intolerable gaps between the clustered ablation sites. In the present example, processor 42 checks whether any of the gaps is larger than the ADT threshold but smaller than the OOG threshold. Alternatively, however, any other suitable alerting criterion can be used for identifying a gap as intolerable.

If no intolerable gaps were found, the method loops back to step 200 above. If one or more gaps were found to be intolerable, processor 42 marks the identified gaps on display 46, at a marking step 220. Any suitable visual means can be used for this purpose. The method then loops back to step 200 above, in which the physician optionally forms additional ablation sites 100 in the identified gaps.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   receiving locations of multiple ablation sites formed on a surface of a heart;
   measuring distances among at least some of the ablation sites based on the locations;
   based on the distances, determining a second ablation site that is a closest neighbor to a first ablation site;
   identifying a gap between the first and second ablation sites and;
   determining whether the gap that meets an alerting criterion; and
   indicating the identified gap to an operator;
   wherein when the gap is determined to meet the alerting criterion, the step of indicating comprises highlighting to the operator that the identified gap is a gap that has been determined to meet the alerting criterion.

2. The method according to claim 1, wherein the step of determining whether the gap meets an alerting criterion comprises identifying whether the gap is larger than a first threshold but smaller than a second threshold;
   wherein when the gap is determined to be larger than a first threshold but smaller than the second threshold, the step of indicating comprises highlighting to the operator that the identified gap is a gap that has been determined to meet the alerting criterion.

3. The method according to claim 1, wherein measuring the distances comprises scaling a distance between the first and second ablation sites by a scaling factor that depends on an ablation quality associated with one or both of the first and second ablation sites.

4. The method according to claim 1, wherein measuring the distances comprises clustering the ablation sites into groups by connecting adjacent ablation sites whose distances are smaller than a first threshold, and wherein the step of determining whether the gap meets an alerting criterion comprises identifying separations between at least a first group comprising the first ablation site and a second group comprising the second ablation site that are smaller than a second threshold.

5. The method according to claim 4, wherein clustering the ablation sites comprises iteratively calculating the distances from a given cluster to one or more of the ablation sites, and adding an ablation site to the given cluster upon finding that a distance from the ablation site to the given cluster is smaller than the first threshold.

6. The method according to claim 1, wherein measuring the distances comprises assessing the distances depending on parameters of an ablation signal used for forming the ablation sites.

7. The method according to claim 1, wherein measuring the distances comprises assessing the distances depending on sizes of the ablation sites.

8. The method according to claim 1, wherein the step of determining whether the gap meets an alerting criterion comprises determining whether the gap is:
   (a) smaller than a first threshold;
   (b) larger than the first threshold, but smaller than a second threshold; or
   (c) larger than the second threshold;
   wherein when the gap is determined to be larger than the first threshold but smaller than the second threshold, the step of indicating comprises highlighting to the operator that the identified gap is a gap that has been determined to meet the alerting criterion.

9. The method of claim 8, wherein when the gap is determined to be less that the first threshold, the step of indicating comprises displaying the first and second ablation sites connected by a line;
   wherein when the gap is determined to be larger than the first threshold but smaller than the second threshold, the step of indicating comprises displaying the first and second ablation sites connected by a bold line to highlight to the operator that the identified gap is a gap that has been determined to meet the alerting criterion; and
   wherein when the gap is determined to be greater that the second threshold, the step of indicating comprises displaying no connection between the first and second ablation sites.

10. A system, comprising:
   an interface, which is configured to receive locations of multiple ablation sites formed on a surface of a heart;
   a processor, which is configured to:
      measure distances among at least some of the ablation sites based on the locations and to determine a second ablation site that is a closest neighbor to a first ablation site,
      to identify a gap between the first and second ablation sites, and
      to determine whether the gap meets an alerting criterion; and
   a display to indicate the identified gaps to an operator;
   wherein when the gap is determined to meet the alerting criterion, the display highlights the gap to the operator to indicate that the identified gap is a gap that has been determined to meet the alerting criterion.

11. The system according to claim 10, wherein the processor is configured to determine whether the gap meets an alerting criterion by detecting the gaps that are larger than a first threshold but smaller than a second threshold;
   wherein when the gap is determined to be larger than a first threshold but smaller than the second threshold, the step of indicating comprises highlighting to the operator that the identified gap is a gap that has been determined to meet the alerting criterion.

12. The system according to claim 10, wherein the processor is configured to scale a distance between the first and second ablation sites by a scaling factor that depends on an ablation quality associated with one or both of the first and second ablation sites.

13. The system according to claim 10, wherein the processor is configured to cluster the ablation sites into groups by connecting adjacent ablation sites whose distances are smaller than a first threshold, and to identify separations between at least a first group comprising the first ablation site and a second group comprising the second ablation site that are smaller than a second threshold.

14. The system according to claim 13, wherein the processor is configured to cluster the ablation sites by iteratively calculating the distances from a given cluster to one or more of the ablation sites, and adding an ablation site to the given cluster upon finding that a distance from the ablation site to the given cluster is smaller than the first threshold.

15. The system according to claim 10, wherein the processor is configured to assess the distances depending on parameters of an ablation signal used for forming the ablation sites.

16. The system according to claim 10, wherein the processor is configured to assess the distances depending on sizes of the ablation sites.

17. The system according to claim 10, wherein to determine whether the gap meets an alerting criterion the processor is configured to determine whether the gap is:
   (a) smaller than a first threshold;
   (b) larger than the first threshold, but smaller than a second threshold; or
   (c) larger than the second threshold;
   wherein when the gap is determined to be larger than the first threshold but smaller than the second threshold, the display highlights to the operator that the identified gap is a gap that has been determined to meet the alerting criterion.

18. The system of claim 17, wherein when the gap is determined to be less that the first threshold, the display indicates the first and second ablation sites connected by a line;
   wherein when the gap is determined to be larger than the first threshold but smaller than the second threshold, the display indicates the first and second ablation sites connected by a bold line to highlight to the operator that the identified gap is a gap that has been determined to meet the alerting criterion; and
   wherein when the gap is determined to be greater that the second threshold, the display indicates no connection between the first and second ablation sites.

* * * * *